United States Patent
Peiro Rodríguez

(10) Patent No.: US 10,212,909 B2
(45) Date of Patent: Feb. 26, 2019

(54) ARTICHOKE VARIETY NUN 04455 ARA

(71) Applicant: Nunhems B.V., AB Nunhem (NL)

(72) Inventor: Maria Teresa Peiro Rodríguez, Pilar de la Horadada (ES)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/815,760

(22) Filed: Nov. 17, 2017

(65) Prior Publication Data

US 2018/0070546 A1 Mar. 15, 2018

(30) Foreign Application Priority Data

Nov. 17, 2016 (EP) ..................... 16199333

(51) Int. Cl.
*A01H 5/02* (2018.01)
*A01H 6/14* (2018.01)
*A01H 5/12* (2018.01)

(52) U.S. Cl.
CPC .............. *A01H 6/14* (2018.05); *A01H 5/02* (2013.01); *A01H 5/12* (2013.01)

(58) Field of Classification Search
CPC ...................................... A01H 6/14
See application file for complete search history.

(56) References Cited

FOREIGN PATENT DOCUMENTS

WO 2013182646 A1 12/2013
WO 2014076249 A1 5/2014

OTHER PUBLICATIONS

Perez-Garcia et al 2000 Free Radical Research 33: 661-665.*
Bedini, Laura, et al., Plant tissue cultures from four Tuscan globe artichoke cultivars, Cent. Eur. J. Biol., 2012, pp. 680-689, vol. 7, No. 4, DOI: 10.2478/s11535-012-0064-x.
Martin, Eugenia, et al., Identification of markers linked to agronomic traits in globe artichoke, Australian Journal of Crop Science, 2008, pp. 43-46, vol. 1, No. 2, ISSN: 1835-2707.
Pecaut, P., et al., Intérêt des plants sains d'artichaut régénérés par la culture << in vitro >>, Revue Horticole, 1985, pp. 21-26, No. 256.
Pisanu, A.B., et al., Yield and Biometric Characteristics of 9 Clones Selected from the Population of "*Spinoso sardo*" Artichokes, ISHS 2004, pp. 83-89, Acta Hort. 660.
Ryder, Edward J., et al., The Globe Artichoke (*Cynara scolymus* L.), Hort Science, Oct. 1983, pp. 646-653, vol. 18.
Vos, Pieter, et al., AFLP: a new technique for DNA fingerprinting, Nucleic Acid Research, 1995, pp. 4407-4414, vol. 23, No. 21.
Wijnker, Erik, et al., Hybrid recreation by reverse breeding in *Arabidopsis thaliana*, Nature Protocols, 2014, pp. 761-772, vol. 9, No. 4, DOI: 10.1038/nprot.2014.049.
UPOV, Guidelines for the Conduct of Tests for Distinctness, Uniformity and Stability—Artichoke, Cardoon TG/184/4 (Geneva, last revised 2011 )world wide web at upov.int/ under edocs/tgdocs/en/tg184.pdf, pp. 1-46.
USDA, Objective Description of Variety—Artichoke (*Cynara scolymus* L.) world wide web at ams.usda.gov/under resources/st470-artichoke, Jun. 2015, pp. 1-3.

* cited by examiner

*Primary Examiner* — David H Kruse
(74) *Attorney, Agent, or Firm* — Arent Fox LLP

(57) ABSTRACT

The invention provides a new and distinct hybrid variety of Artichoke, NUN 04455 ARA, as well as seeds and plants and flower heads thereof.

17 Claims, No Drawings

ARTICHOKE VARIETY NUN 04455 ARA

CROSS REFERENCE TO RELATED APPLICATION

This application claims the benefit of European Patent Application No. 16199333.2, filed Nov. 17, 2016, the contents of which are herein incorporated by reference in their entirety.

FIELD OF THE INVENTION

The present invention relates to the field of plant breeding and, more specifically, to the development of NUN 04455 ARA (also designated as NUN 04455 or NUN 04455 F1 or NUN 04455 hybrid). The invention further relates to vegetative reproductions of NUN 04455 ARA, methods for tissue culture of NUN 04455 ARA and regenerating a plant from such a tissue culture and also to phenotypic variants of NUN 04455 ARA.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate etc.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce it uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential. One crop species which has been subject to such breeding programs and is of particular value is the Artichoke.

Artichoke (*Cynara cardunculus* var. *scolymus*) is grown primarily for its edible flower head or bud is naturally a diploid (2n=34) outcrossing species. The two main types of artichoke grown commercially today in the United States have green or purple flower heads, which are large or medium size. Spined and white artichoke varieties are also known.

Artichoke cultivars have traditionally been bred as clones, using vegetative propagation (planting of basal stumps or suckers), because seed populations were not uniform enough for cultivation. In recent years seed propagated hybrid cultivars have been developed which do have good uniformity, such as Madrigal F1, Concerto F1 and others. These hybrids are produced from true breeding inbred parental lines. The varieties and production methods are typically adapted to the end use, which is typically fresh market or processing for Artichoke. Artichoke production has risen to 1.8 Mt in 2013 (FAOSTAT, 2013) with an approximate value of US$600 million.

The shift to seed-planted varieties (rather than vegetative cultivation) has enabled artichoke to be grown as an annual crop, although seed-planted varieties can also be grown as perennials. Seed-planted varieties are cost and labor saving, because seeds are sown mechanically. Also yields and quality are much higher, probably to some extent due to the fact that direct-seeded plants produce long taproots, which penetrate deeper into the soil than the vegetative plantations. Hybrid vigor also plays a role in improved yields, as does the better pest and disease control of annually seeded crops. Although a number of (seed-planted) hybrid varieties exist, there is still a need for new, high yielding, uniform hybrids with good head quality. Such plants would benefit farmers and consumers alike by improving crop yields and/or quality.

SUMMARY OF THE INVENTION

In an aspect of the invention, a seed of Artichoke variety NUN 04455 ARA is provided, wherein a representative sample of said seed has been deposited under Accession Number NCIMB 42843. The invention also provides for a plurality of seeds of NUN 04455 ARA. The Artichoke seed of NUN 04455 ARA may be provided as an essentially homogeneous population of Artichoke seed. Therefore, seed of the invention may be defined as forming at least about 97% of the total seed, including at least about 98%, 99% or more of the seed. The population of seed of NUN 04455 ARA may be particularly defined as being essentially free from other seed. The seed population may be grown into plants to provide an essentially homogeneous population of Artichoke plants according to the invention.

Also encompassed is a plant grown from a seed of Artichoke variety NUN 04455 ARA and a plant part thereof. In another aspect the invention provides for a hybrid variety of Artichoke called NUN 04455 ARA. The invention also provides for a progeny of NUN 04455 ARA. Especially, a plant or a progeny retaining all or all but one, two or three of the "distinguishing characteristics" or all or all but one, two or three of the "morphological and physiological characteristics" of NUN 04455 ARA referred to herein, is encompassed herein as well as methods for producing that plant or progeny.

In one aspect, a plant or a progeny of the invention have all the physiological and morphological characteristics of variety NUN 04455 ARA when grown under the same environmental conditions. In another aspect such a plant or such progeny have all or all but one, two or three of the physiological and morphological characteristics of NUN 04455 ARA when measured under the same environmental conditions and evaluated at significance levels of 1%, 5% or 10% significance (which can also be expressed as a p-value) wherein a representative sample of seed of variety NUN 04455 ARA has been deposited under Accession Number NCIMB 42843. In a second aspect, a plant or a progeny of the invention have all the physiological and morphological characteristics of variety NUN 04455 ARA when grown under the same environmental conditions. In another aspect such a plant or such progeny have all or all but one, two or three of the physiological and morphological characteristics as listed in Table 1 and/or 2 and/or 3 for variety NUN 04455 ARA when measured under the same environmental conditions and evaluated at significance levels of 1%, 5% or 10% significance.

Also a plant part obtained from variety NUN 04455 ARA is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, "ovoli", a cutting, a seed, a part of a seed, seedcoat or another maternal tissue which is part of a seed grown on said varieties, hypocotyl, cotyledon, a scion, a stock, a rootstock, a pistil, an anther, a flower head (also known as bud or shortened to head) or a apart thereof or and a flower or a part thereof. flower heads are particularly important plant parts. In a further embodiment, the plant part obtained from variety NUN 04455 ARA is a cell, optionally a cell in a cell or tissue culture. That cell may be grown into a plant of NUN 04455 ARA.

The invention also provides a cell culture of NUN 04455 ARA and a plant regenerated from NUN 04455 ARA, which plant has all the characteristics of NUN 04455 ARA when grown under the same environmental conditions, as well as methods for regenerating NUN 04455 ARA. Alternatively, a regenerated plant may have one characteristic that is different from NUN 04455 ARA.

Further, a vegetatively propagated plant of variety NUN 04455 ARA is provided having all or all but one, two or three of the morphological and physiological characteristics NUN 04455 ARA when grown under the same environmental conditions.

Further, an Artichoke flower head produced on a plant grown from a seed of NUN 04455 ARA is provided.

In still another aspect, a seed growing or grown on a plant of NUN 04455 ARA is provided (i.e. produced after pollination of the flower of NUN 04455 ARA).

Definitions

All patent and non-patent documents cited herein are incorporated by reference in their entirety.

"Artichoke" refers herein to plants of the species *Cynara cardunculus* var. *scolymus*. The most commonly eaten part of an Artichoke is the flower head. Certain extracts of artichoke are also used in the pharmaceutical field.

"Cultivated Artichoke" refers to plants of *Cynara cardunculus* i.e. varieties, breeding lines or cultivars of the species *Cynara cardunculus*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of Artichoke.

"Flower head" refers to immature flower heads harvested or on the plant. The "central flower head" refers to the terminal flower head produced on the central, main stem. Other flower heads are produced on lateral branches. The flower head, also known as globe, head, capitulate or flower bud, comprises spines, bracts (sometimes divided in inner and outer bracts), young flowers, heart, capitulum base or bottom and stalks or peduncles. "Heart" is the edible part of the flower head comprising or consisting of the fleshy receptacle (or a part thereof) with the fleshy base of the inner bracts (or parts thereof). "Bottom" is the edible fleshy lower part of the heart.

The term "multibranching" or "multi-branching" plant or "plant exhibiting a multibranching growth habit" refers to an artichoke plant that develops, in addition to the primary and secondary stems of the normal plant, additional (lateral) branches that start growing on the leaf axil of the (mature) leaves. More specifically, these additional branches start growing on the leaf axil of leaves on the lower part of the plant whereas the normal secondary branches grow from the top part of the plant. These additional branches are herein referred to as M-branch(es).

The multibranching trait is disclosed in EP 16199333.2 which is incorporated by reference.

The term "number of heads" relates to the total number of heads an artichoke plant produces in one year (in one growing season). It is the sum of all heads growing on a plant in one season. In other words, it is the number of primary head and secondary head(s) and heads growing on M-branch(es) (i.e. M-heads), including heads growing on FM-branch(es) (i.e. FM-heads), and tertiary head(s) and optionally further level heads. The number of heads can be counted per plant. However, preferably the number of heads is counted as an average number of multiple replications of plants of the same variety in order to get statistically relevant data (which may be referred to as "average number of heads"). For example the average number of heads in a population of 5 or more plants of the same variety (e.g. 6, 7, 8, 9, 10, 15, 20 or even more) plants. It is understood that a person skilled in the art of plant breeding will know what number of plants should be to get reliable data.

An "increase in the number of heads" or an "increased number of heads" is defined as the average number of heads per plant of the same line or variety, produced per year or growing season, that is higher than the average number of heads per plant produced by a comparison line or variety in the same period when grown under the same conditions. Such a (statistically) significantly higher average number of heads per *Cynara cardunculus* var. *scolymus* plant line or variety can be observed when comparing a *Cynara cardunculus* var. *scolymus* plant comprising the multibranching trait in homozygous or heterozygous form with a control line or variety lacking the multibranching trait. Such a control line can be an isogenic plant to the plant comprising the multibranching trait. Alternatively, the control plant can be selected from the group consisting of commercial artichoke varieties Madrigal and Symphony (produced and sold by Bayer CropScience Vegetable Seeds/Nunhems). It is understood that such a comparison should be done between plants that have grown under the same environmental conditions in order to exclude effects of soil type, humidity, temperature, etc.

The terms "Artichoke plant designated NUN 04455 ARA", "NUN 04455 ARA", "NUN 04455", "NUN 04455 F1", "04455 ARA", Nun 55 ARA' or "Artichoke 04455" are used interchangeably herein and refer to an Artichoke plant of variety NUN 04455 ARA, representative seed of which having been deposited under Accession Number NCIMB 42843.

A "seed of NUN 04455 ARA" refers to an Artichoke seed which can be grown into a plant of NUN 04455 ARA wherein a representative sample of viable seed of NUN 04455 ARA has been deposited under Accession Number NCIMB 42843. A seed can be in any stage of maturity, for example a mature, viable seed, or an immature, non-viable seed. A seed comprises an embryo and maternal tissues.

An "embryo of NUN 04455 ARA" refers to an "F1 hybrid embryo" as present in a seed of NUN 04455 ARA, a representative sample of said seed of NUN 04455 ARA having been deposited under Accession Number NCIMB 42843.

A "seed grown on NUN 04455 ARA" refers to a seed grown on a mature plant of NUN 04455 ARA or inside a fruit of NUN 04455 ARA. The "seed grown on NUN 04455 ARA" contains tissues and DNA of the maternal parent, NUN 04455 ARA. The "seed grown on NUN 04455 ARA" contains an F2 embryo. When said seed is planted, it grows into a first generation progeny plant of NUN 04455 ARA.

"Tissue culture" or "cell culture" refers to a composition comprising isolated cells of the same or a different type or a collection of such cells organized into parts of a plant. Tissue culture of various tissues of artichoke and regeneration of plants therefrom is well known and widely published (see, e.g., Pecaut et al. 1985, Revue Horticuole 256: 21-26); Bedini et al, 2012). Similarly, the skilled person is well-aware how to prepare a "tissue culture" or "cell culture".

"UPOV descriptors" are the plant variety descriptors described for Artichoke in the "Guidelines for the Conduct of Tests for Distinctness, Uniformity and Stability—Artichoke, Cardoon TG/184/4 (Geneva, last revised 2011), as published by UPOV (International Union for the Protection of New Varieties and Plants) and which can be downloaded from the world wide web at upov.int/ under edocs/tgdocs/en/tg184.pdf and is herein incorporated by reference in its entirety.

"USDA descriptors" are the plant variety descriptors for Artichoke as described in the document titled "OBJECTIVE DESCRIPTION OF VARIETY—Artichoke (*Cynara scolymus* L.)" as published by the US Department of Agriculture, Agricultural Marketing Service, Plant Variety Protection Office, Beltsville, Md. 20705 and which can be downloaded from the world wide web at ams.usda.gov/ under resources/st470-artichoke "Non-USDA descriptors" are other descriptors suitable for describing Artichoke.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking, Surrey GU236QB, UK, e.g., the RHS colour chart: 2007 (The Royal Horticultural Society, charity No: 222879, PO Box 313 London SW1P2PE.

As used herein and except as otherwise indicated, the term "plant" includes the whole plant or any part thereof, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an embryo, a petiole, a shoot or a part thereof, a stem or a part thereof, a root or a part thereof, a root tip, "ovoli", a cutting, a seed, a part of a seed, seed coat or another maternal tissue which is part of a seed grown on a variety of the invention, hypocotyl, cotyledon, a scion, a graft, a stock, a rootstock, a pistil, an anther, a flower head (also known as bud) or a part thereof, a spine, a bract, a heart, a bottom or and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 04455 ARA. An F2 progeny produced from self-pollination of NUN 04455 ARA will thus comprise two sets of chromosomes derived from NUN 04455 ARA, while an F2 progeny derived from cross-fertilization of NUN 04455 ARA will comprise only one set of chromosomes from NUN 04455 ARA and the other set of chromosomes from the other parent.

"Harvested plant material" refers herein to plant parts (e.g. a flower head detached from the whole plant) which have been collected for further storage and/or further use.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 and/or 3 or "all or all but one, two or three of the physiological and morphological characteristics" of Table 1 and/or 2 and/or 3.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 04455 ARA may have one or more (or all) of the essential physiological and/or morphological characteristics of said variety listed in Table 1 and/or 2 and/or 3, as determined at the 5% significance level (i.e. $p<0.05$) when grown under the same environmental conditions.

"Distinguishing characteristics" or "distinguishing morphological and/or physiological characteristics" refers herein to the characteristics which distinguish (i.e. are different) between the new variety and other Artichoke varieties, such as the Reference Variety, when grown under the same environmental conditions. The distinguishing characteristics between NUN 04455 ARA and Reference Variety are described elsewhere herein and also can be seen in Table 1 and/or Table 2 and/or 3. When comparing NUN 04455 ARA with different varieties, the distinguishing characteristics will be different. In one aspect, the distinguishing characteristics may therefore include at least one, two, three or more (or all) of the characteristics listed in Table 1 and/or 2 and/or 3. All numerical distinguishing characteristics are statistically significantly different at $p<0.05$ between NUN 04455 ARA and the other variety, e.g. Reference Variety.

Thus, an Artichoke plant "comprising the distinguishing characteristics of NUN 04455 ARA (such as a progeny plant) refers herein to a plant which does not differ significantly from said variety in the distinguishing characteristics above. Therefore in one aspect a plant (such as a progeny plant of NUN 04455 ARA) is provided which does not differ significantly from NUN 04455 ARA in the distinguishing characteristics above.

Similarity and differences between two different plant lines or varieties can be determined by comparing the number of morphological and/or physiological characteristics (e.g. the characteristics as listed in Table 1 and/or 2 and/or 3) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated Artichoke" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method. For artichoke, vegetative propagation comprises propagation through ovoli (Ryder et al., 1983, Hort Science 18: 646-653).

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all Artichoke flower heads harvested per plant or per hectare of a particular line or variety. It is understood that "yield" can be expressed as weight or number of Artichoke heads. Yield per hectare can be obtained by multiplying the number of plants per hectare times the "yield per plant". "Marketable yield" means the total weight of all marketable Artichoke heads.

"Harvest maturity" is referred to as the stage at which an Artichoke head is ripe or ready for harvest or the optimal time to harvest the head for the market, for processing or for consumption.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one Artichoke line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 04455 ARA. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another Artichoke plant of the same variety or another variety or (breeding) line, or with wild Artichoke plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration. Thus, a plant of NUN 04455 ARA is the male parent, the female parent or both of a first generation progeny of NUN 04455 ARA. Progeny may have all the physiological and morphological characteristics of variety NUN 04455 ARA when grown under the same environmental conditions and/or progeny may have (be selected for having) one or more of the distinguishing characteristics of the artichoke of the invention. Using common breeding methods such as backcrossing or recurrent selection, one or more specific characteristics may be introduced into said variety, to provide or a plant comprising all but 1, 2, or 3 or more of the morphological and physiological characteristics of NUN 04455 ARA (as listed in Table 1 and/or 2 and/or 3)

The terms "gene converted" or "conversion plant" or "single locus converted plant" in this context refer to Artichoke plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of backcrossing, wherein essentially all of the desired morphological and physiological characteristics of an Artichoke variety are recovered in addition to the characteristics of the single locus having been transferred into the variety via the backcrossing technique and/or by genetic transformation and/or by mutation. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for Artichokes described herein. The mean, if not indicated otherwise within this application, refers to the arithmetic mean of measurements on at least 10 different, randomly selected plants of a variety or line.

DETAILED DESCRIPTION

The present invention relates to a plant of NUN 04455 ARA wherein a representative sample of seeds of said variety was deposited under the Budapest Treaty, with Accession number NCIMB 42843.

NUN 04455 ARA is a multibranching artichoke plant, i.e. comprising in its genome a genetic determinant that confers a multibranching growth habit. Plants with this multibranching growth habit produce (many) more lateral branches (referred to as M-branches) and flower heads per plant. A lateral branch develops one main head which is comparable to the development of the secondary head on the main stem on the plant. In addition, a lateral branch may develop additional heads. As a result of the altered overall plant structure caused by this genetic determinant, the average number of heads per plant increases compared to plants lacking this genetic determinant.

NUN 04455 ARA shows an increase in the number of heads of at least 5% as compared to an *Cynara cardunculus* var. *scolymus* plant not carrying said genetic determinant.

NUN 04455 ARA comprises in its genome a genetic determinant that confers a multibranching growth habit, wherein the plant produces an average number of heads of at least 17 heads. In one aspect of the invention, said genetic determinant comprises (preferably is) the dominant multibranching allele (M), wherein samples of seed comprising said allele have been deposited under deposit number NCIMB 42843. NUN 04455 ARA also comprises the dominant enhanced multibranching allele (E), wherein a sample of seed comprising said allele has been deposited under deposit number NCIMB 42843

NUN 04455 ARA comprises one or more QTLs selected from the group consisting of MB_1.1 located on chromosome 1 and MB_3.1 located on chromosome 3. In still another embodiment, said genetic determinant has both the QTL MB_1.1 located on chromosome 1 and the QTL MB_3.1 located on chromosome 3.

The present invention also relates to a seed of Artichoke variety NUN 04455 ARA, wherein a representative sample of said seed was deposited under the Budapest Treaty, with Accession number NCIMB 42843.

In another aspect, the invention provides for an Artichoke plant part of variety NUN 04455 ARA, preferably a head, a representative sample of seed from said variety has been deposited under the Budapest Treaty, with Accession number NCIMB 42843.

A seed of hybrid variety NUN 04455 ARA is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into containers of any size or type (e.g., bags, cartons, cans, etc.). The seed may be disinfected, primed and/or treated with various compounds, such as seed coatings or crop protection compounds. The seed produces a plant of NUN 04455 ARA.

Also provided is a plant of Artichoke variety NUN 04455 ARA, or a flower head or other plant part thereof, produced from a seed, wherein a representative sample of said seeds has been deposited under the Budapest Treaty, with Accession Number NCIMB 42843.

Also a plant part obtained from variety NUN 04455 ARA is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, "ovoli", a cutting, a seed, a part of a seed, seedcoat or another maternal tissue which is part of a seed grown on said varieties, hypocotyl, cotyledon, a scion, a stock, a rootstock, a pistil, an anther, a flower head or a apart thereof, a spine, a bract, a heart, a bottom and a flower or a part thereof. Flower heads are particularly important plant parts. In a further embodiment, the plant part obtained from variety NUN 04455 ARA is a cell, optionally a cell in a cell or tissue culture. That cell may be grown into a plant of NUN 04455 ARA. A part of a variety of the invention, i.e. NUN 04455 ARA (or of progeny NUN 04455 ARA or of a plant having all physiological and/or morphological characteristics but one, two or three which are different from those of NUN 04455 ARA) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is an Artichoke flower head or part thereof, in particular a spine, a bract, a heart or a bottom and/or an extract or another plant part described herein comprising at least one cell of NUN 04455 ARA. The food or feed product may be fresh or processed, e.g., dried, grinded, powdered, pickled, chopped, cooked, roasted, in a sauce, in a sandwich, pasted, puréed or concentrated, juiced, pickled, canned, preserved in oil or other preservatives, steamed, boiled, fried, grilled, blanched and/or frozen, etc.

Such a plant part of NUN 04455 ARA can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered Artichoke flower head or part thereof, in particular a spine, a bract, a heart or a bottom from NUN 04455 ARA or from progeny of said varieties, or from a derived variety, such as a plant having all but one, two or three physiological and/or morphological characteristics of NUN 04455 ARA.

In a preferred embodiment, the invention provides for an Artichoke flower head of variety NUN 04455 ARA, or a part of a head of said variety in particular a spine, a bract, a heart or a bottom. The heads can be in any stage of maturity, for example immature or mature, or in a preferred embodiment harvest-stage heads. In another embodiment, the invention provides for a container comprising or consisting of a plurality of harvested Artichoke flower heads or parts of heads of said variety, or heads of progeny thereof, or heads of a derived variety. For example, containers such as cans, boxes, crates, bags, cartons, Modified Atmosphere Packagings, films (e.g. biodegradable films), etc. comprising a plant or a parts of a plant (fresh and/or processed) described herein or a seed of NUN 04455 ARA are also provided herein.

In another embodiment the plant, plant part or seed of NUN 04455 ARA is inside a container, For example, containers such as cans, boxes, crates, bags, cartons, Modified Atmosphere Packagings, films (e.g. biodegradable films), etc. comprising a plant or a part of a plant (fresh and/or processed) of NUN 04455 ARA or a seed of NUN 04455 ARA are also provided herein. In a preferred embodiment, the container comprises a plurality of seeds of NUN 04455 ARA, or a plurality of plant parts of NUN 04455 ARA.

The invention further provides an Artichoke plant which does not differ from the plant of the invention as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 04455 ARA. Such a tissue culture can be for example be grown on plates or in liquid culture, or be frozen for long term storage. The cells of NUN 04455 ARA used to start the culture can be selected from any plant part suitable for vegetative reproduction, or in a preferred embodiment can be selected from embryos, meristems, cotyledons, hypocotyl, pollen, leaves, anthers, roots, root tips, "ovoli", pistil, petiole, flower head, spines, bracts, hearts, bottoms, flower, fruit, seed, stem and stalks of NUN 04455 ARA. In another preferred embodiment, the tissue culture does not contain somaclonal variation or has reduced somaclonal variation. The skilled person is familiar with methods to reduce or prevent somaclonal variation, including regular reinitiation.

In one embodiment the invention provides an Artichoke plant regenerated from the tissue or cell culture of NUN 04455 ARA, wherein the regenerated plant is not significantly different from NUN 04455 ARA in all, or all but one, two or three, of the physiological and morphological characteristics (determined at the 5% significance level when grown under the same environmental conditions). Optionally, the plant has one, two or three the physiological and morphological characteristics that are effected by a mutation or by transformation. In another embodiment, the invention provides an Artichoke plant regenerated from the tissue or cell culture of NUN 04455 ARA, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

An Artichoke according to the invention, such as NUN 04455 ARA, or its progeny, or a plant having all physiological and/or morphological characteristics but one, two or three which are different from those of NUN 04455 ARA, can also be reproduced using vegetative reproduction methods. Therefore, the invention provides for a method of producing a plant, or a part thereof, of variety NUN 04455 ARA, comprising vegetative propagation of said variety. Vegetative propagation comprises regenerating a whole plant from a plant part of variety NUN 04455 ARA (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 04455 ARA. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 04455 ARA.

In a preferred embodiment, the part of the plant to be propagated is is a cutting, a cell culture, a tissue culture, a "stump" (basal stem piece with attached root sections or a rooted section of the crown), a sucker, a shoot or offshoot or ovoli derived from NUN 04455 ARA (see Ryder et al., 1983, Hort Science 18: 646-653).

The invention also provides for a vegetatively propagated plant of variety NUN 04455 ARA (or from progeny of said variety or from or a plant having all but one, two or three physiological and/or morphological characteristics of NUN 04455 ARA) wherein the plant has all of the morphological and physiological characteristics of NUN 04455 ARA when the characteristics are determined at the 5% significance level for plants grown under the same conditions. In another embodiment, the propagated plant has all but one, two or three of the morphological and physiological characteristics of NUN 04455 ARA when the characteristics are determined at the 5% significance level for plants grown under the same conditions. A part of said propagated plant or said propagated plant with one, two or three differences is also included.

In an embodiment, the invention provides a method for producing an Artichoke plant, comprising the steps of:
  a. Growing a plant of claim 1 until it develops at least one flower head.
  b. Collecting the flower head of step a)
Preferably, the flower head is collected at harvest maturity. In another embodiment, the flower head is collected manually. A plant of NUN 04455 ARA can be produced by seeding directly in the soil (e.g., field) or by germinating the seeds in controlled environment conditions (e.g., greenhouses) and optionally then transplanting the seedlings into the field. Furthermore, a plant of NUN 04455 ARA can be produced by vegetative propagation or propagation through tissue culture. For example, the seed can be sown into prepared seed beds where they will remain for the entire production the crop.

In still another aspect the invention provides a method of producing an Artichoke plant, comprising crossing a plant of Artichoke NUN 04455 ARA with a second Artichoke plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent Artichoke plant, often in proximity so that pollination will occur, for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 04455 ARA one or more times, and selecting a progeny plant from said selfing. In one aspect the progeny plant retains all the distinguishing characteristics of NUN 04455 ARA described above. In a different embodiment the progeny plant comprises all (or all but one, two or three) of the physiological and morphological characteristic of NUN 04455 ARA of Table 1 and/or 2 and/or 3. In a further embodiment the progeny plant comprises all physiological and morphological characteristic of NUN 04455 ARA when grown under the same environmental conditions.

In other aspects, the invention provides a progeny plant of variety NUN 04455 ARA such as a progeny plant obtained by further breeding that variety. Further breeding with said variety includes selfing that variety one or more times and/or cross-pollinating that variety with another Artichoke one or more times. In particular, the invention provides for a progeny plant that retains all the essential morphological and physiological characteristics of NUN 04455 ARA or, in another embodiment, a progeny plant that retains all, or all but one, two or three, of the morphological and physiological characteristics of NUN 04455 ARA, optionally all or all but one, two or three of the characteristics as listed in Table 1 and/or 2 and/or 3 determined at the 5% significance level for numerical characteristics, when grown under the same environmental conditions. In a preferred embodiment, the progeny is a first generation progeny, i.e. the ovule or the pollen (or both) used in the crossing is an ovule or pollen of variety NUN 04455 ARA, i.e. the pollen comes from an anther of NUN 04455 ARA and the ovule comes from an ovary of NUN 04455 ARA. In another aspect, the invention provides for a vegetative reproduction of the variety and a plant having all, or all but 1, 2, or 3 of the physiological and morphological characteristics of NUN 04455 ARA (e.g. as listed in Table 1 and/or 2 and/or 3).

The morphological and/or physiological differences between two different individual plants of the invention (e.g. between NUN 04455 ARA and a progeny of NUN 04455 ARA) or between a plant of NUN 04455 ARA or progeny of said variety, or a plant having all, or all but 1, 2, or 3, of the physiological and morphological characteristics of NUN 04455 ARA (or all, or all but 1, 2, or 3 of the characteristics as listed in Table 1 and/or 2 and/or 3) and another known variety can easily be established by growing said variety next to each other or next to the other variety (in the same field, under the same environmental conditions), preferably in several locations which are suitable for said Artichoke cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18'807", USA, whereby various characteristics, for example maturity, days from seeding to harvest, plant habit, plant attitude, leaf size, leaf shape, leaf color, numbers of primary and secondary flower heads, primary and secondary head shape and size, bract shape and size, bract color, floret color and size, number of petals, anthocyanin, disease resistance and pest resistance can be measured and directly compared for species of Artichoke. Thus, the invention comprises Artichoke plant having one, two or three physiological and/or morphological characteristics which are different from those of the plant of claim 1 and which otherwise has all the physiological and morphological characteristics of the plant of claim 1, when determined at the 5% significance level for plants grown under the same environmental conditions. In a preferred embodiment, the different characteristic is effected by a mutation or by transformation.

The morphological and physiological characteristics (and the distinguishing characteristics) of NUN 04455 ARA are provided in the Examples. Encompassed herein is also a plant obtainable from NUN 04455 ARA (e.g. by selfings and/or crossing and/or backcrossing with said variety and/or progeny of said variety) comprising all or all but one, two or three of the physiological and morphological characteristics of NUN 04455 ARA listed in Table 1 and/or 2 and/or 3 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of flower heads can be compared, such as storage holding quality, post-harvest firmness, and color can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In a preferred embodiment, the invention provides for an Artichoke flower head of variety NUN 04455 ARA, or a part of a head of said varieties such as spines, bracts (sometimes divided in inner and outer bracts), young flowers, heart, capitulum base or bottom and stalks or peduncles. In another embodiment, the invention provides for a container comprising or consisting of a plurality of harvested Artichoke heads or parts thereof, or heads of progeny thereof.

In yet a further embodiment, the invention provides for a method of producing a new Artichoke plant. The method comprises crossing a plant of the invention i.e. NUN 04455 ARA, or a plant comprising all but 1, 2, or 3 of the morphological and physiological characteristics of said variety (as listed in Table 1 and/or 2 and/or 3), or a progeny plant thereof, either as male or as female parent, with a second Artichoke plant (or a wild relative of Artichoke) one or more times, and/or selfing an Artichoke plant according to the invention i.e. NUN 04455 ARA, or a progeny plant thereof, one or more times, and selecting progeny from said crossing and/or selfing. The second Artichoke plant may for example be a line or variety of the species *Cynara cardunculus* var. *sylvestris* (wild cardoon), *Cynara cardunculus* subsp *cardunculus* (cultivated cardoon), *C. baetica, C. algarbiensis, C. syriaca, C. cornigera, C. cyrenaica, C. humilis* and *C. trournefortii*).

The invention provides for methods of producing plants which retain all the morphological and physiological characteristics of a plant of the invention i.e. NUN 04455 ARA. The invention provides also for methods of producing a plant comprising all but 1, 2, or 3 or more of the morphological and physiological characteristics of NUN 04455 ARA (e.g. as listed in Table 1 and/or 2 and/or 3), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 04455 ARA if its DNA fingerprint is at least 80%, 90%, 95% or 98% identical to the fingerprint of NUN 04455 ARA. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Pisanu et al. ISHS 2004, Acta Hort. 660).

The invention also provides a plant and a variety obtained or selected by applying these methods on NUN 04455 ARA. Such a plant may be produced by crossing and/or selfing, or alternatively, a plant may simply be identified and selected amongst plants of said variety, or progeny of said variety, e.g. by identifying a variant within NUN 04455 ARA or within progeny of said variety (e.g. produced by selfing) which variant differs from NUN 04455 ARA in one, two or three of the morphological and/or physiological characteristics (e.g. in one, two or three distinguishing characteristics), e.g. those listed in Table 1 and/or 2 and/or 3 or others. In one embodiment the invention provides an Artichoke plant having a Jaccard's Similarity index with NUN 04455 ARA of at least 0.8, e.g. at least 0.85, 0.9, 0.95, 0.98 or even at least 0.99.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 04455 ARA is a progeny of said variety, because the seed coat of the seed is a maternal tissue genetically identical to NUN 04455 ARA. In one embodiment, the present invention relates to a seed coat comprising maternal tissue of NUN 04455 ARA. In another embodiment the invention relates to an Artichoke seed comprising a maternal tissue of NUN 04455 ARA.

By crossing and/or selfing also (one or more) single traits may be introduced into the variety of the invention i.e. NUN 04455 ARA (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 04455 ARA by breeding with said variety.

Alternatively, a single trait converted plant or single locus converted plant of NUN 04455 ARA may be produced by the following steps
 a. obtaining a cell or tissue culture of cells of NUN 04455 ARA;
 b. genetically transforming or mutating said cells;
 c. growing the cells into a plant; and
 d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 04455 ARA, progeny of said variety or into a plant comprising all but 1, 2, or 3 or more of the morphological and physiological characteristics of NUN 04455 ARA (e.g. as listed in Table 1 and/or 2 and/or 3). Resistance to one or more of the following diseases or pests is preferably introduced into plants of the invention: Powdery mildew, Verticillium wilt (V. dahliae), Botrytis rot, Curly Dwarf Virus and Bacterial Crown rotartichoke plume moth (Platyptilia caduidactyla), artichoke moth (Gortyna xantheses), aphid resistance, proba bug resistance, two-spotted spider-mite resistance, Chrysanthemum leaf-miner, and Cribate weevil resistance. Other resistance genes, against pathogenic viruses (e.g. Artichoke Latent Virus, ArLV; artichoke mottled crinkle virus, AMCV; Tomato Spotted Wilt Virus, TSWV; Impatiens necrotic spot virus, INSV; Cucumber mosaic virus, CMV), fungi, bacteria or artichoke pests may also be introduced.

Thus, invention also provides a method for developing an Artichoke plant in an Artichoke breeding program, using an Artichoke plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 04455 ARA or progeny of said variety, or a plant comprising all but 1, 2, or 3 or more of the morphological and physiological characteristics of NUN 04455 ARA (e.g. as listed in Table 1 and/or 2 and/or 3), with a different Artichoke plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention also provides an Artichoke plant comprising at least a first set of the chromosomes of Artichoke variety NUN 04455 ARA, a sample of seed of said variety having been deposited under Accession Number NCIMB 42843; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 04455 ARA may also be mutated (by e.g. irradiation, chemical mutagenesis, heat treatment, etc.) and mutated seeds or plants may be selected in order to change one or more characteristics of said variety. Methods such as TILLING may be applied to Artichoke populations in order to identify mutants. Similarly, NUN 04455 ARA may be transformed and regenerated, whereby one or more chimeric genes are introduced into the variety or into a plant comprising all but 1, 2, 3, or more of the morphological and physiological characteristics (e.g. as listed in Table 1 and/or 2 and/or 3). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 04455 ARA, or progeny of said variety, by transforming said variety or progeny of said variety with a transgene that confers the desired trait, wherein the transformed plant retains all or all but one, two or three of the phenotypic and/or morphological and/or physiological characteristics of NUN 04455 ARA or the progeny of said variety and contains the desired trait.

The invention also provides a plant or a cell of a plant comprising a desired trait produced by mutating a plant of variety NUN 04455 ARA or a cell thereof and selecting a plant the desired trait, wherein the mutated plant retains all or all but one of the phenotypic and morphological characteristics of said variety (optionally as described in Table 1 and/or 2 and/or 3) and contains the desired trait and wherein a representative sample of seed of variety NUN 04455 ARA has been deposited under Accession Number NCIMB 42843. In a further embodiment, the desired trait is selected from the group consisting of yield, herbicide tolerance, pest resistance, disease resistance, environmental stress tolerance, modified carbohydrate metabolism, modified protein metabolism and ripening.

The invention also provides a plant having one, two or three physiological and/or morphological characteristics which are different from those of NUN 04455 ARA and which otherwise has all the physiological and morphological characteristics of said variety, wherein a representative sample of seed of variety NUN 04455 ARA has been deposited under Accession Number NCIMB 42843. In particular variants which differ from NUN 04455 ARA in none, one, two or three of the characteristics mentioned in Table 1 and/or 2 and/or 3 are encompassed.

A part of a variety of the invention, i.e. NUN 04455 ARA (or of progeny of said varieties or of a plant having all physiological and/or morphological characteristics but one, two or three which are different from those of said variety) encompasses any cells, tissues, organs obtainable from the seedlings or plants, such as but not limited to: an Artichoke head or a part thereof, a cutting, hypocotyl, cotyledon, seedcoat, pollen and the like. Such parts can be stored and/or processed further. Encompassed are therefore also food or feed products comprising a part of NUN 04455 ARA or a part of progeny of said varieties, or a part of a plant having all but one, two or three physiological and/or morphological characteristics of NUN 04455 ARA, comprising one or more of such parts, optionally processed (such as canned, chopped, cooked, roasted, in a sauce, in a sandwich, pasted, puréed or concentrated, juiced, frozen, dried, pickled, or powdered).

In one aspect a haploid plant and/or a doubled haploid plant of NUN 04455 ARA, or of a plant having all but one, two or three physiological and/or morphological characteristics of NUN 04455 ARA, or progeny of any of these, is encompassed herein.

In yet another aspect haploid plants and/or doubled haploid plants derived from NUN 04455 ARA that, when combined, make a set of parents of NUN 04455 ARA are encompassed herein. Thus the haploid plant and/or the doubled haploid plant of NUN 04455 ARA can be used in a method for generating parental lines of NUN 04455 ARA.

Using methods known in the art like "reverse synthesis of breeding lines" or "reverse breeding", it is possible to produce parental lines for a hybrid plant such as NUN 04455 ARA; where normally the hybrid is produced from the parental lines. Thus, this method introduces a tool that was not available in traditional breeding: a skilled person can take any individual heterozygous plant (called a "phenotypically superior plant" in Example 2 of WO2014076249; NUN 04455 ARA is such a plant) and generate a combination of parental lines (reverse breeding parental lines) that, when crossed, produce the variety NUN 04455 ARA. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi: 10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 04455 ARA) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 04455 ARA when these parental lines are crossed. In still another aspect, the invention relates to a combination of parental lines from which a seed or plant having all physiological and/or morphological characteristics of NUN 04455 ARA (when the characteristics are determined at the 5% significance level for plants grown under the same conditions).

In another aspect, the invention comprises a method for making doubled haploid cells from haploid cells of NUN 04455 ARA.

In another alternative aspect, the invention provides a method of introducing a single locus conversion or single trait conversion or a desired trait into NUN 04455 ARA comprising:

a. obtain a combination of a parental lines of NUN 04455 ARA, optionally through reverse synthesis of breeding lines,
b. introduce a single locus conversion in at least one of the parents of step a;
c. crossing the converted parent with the other parent of step a to obtain seed of NUN 04455 ARA A combination of a male and a female parental line of NUN 04455 ARA can be generated by methods described herein, for example through reverse synthesis of breeding lines.

In an embodiment of the invention, Step b) of the above method—introduce a single locus conversion in at least one of the parents of step a—may be done through the following method:
  i. obtaining a cell or tissue culture of cells of the parental line of NUN 04455 ARA;
  ii. genetically transforming or mutating said cells;
  iii. growing the cells into a plant; and
  iv. optionally selecting plants that contain the single locus conversion, the single trait conversion or the desired trait.

In another embodiment of the invention, Step b) of the above method—introduce a single locus conversion in at least one of the parents of step a—may also be done through the following method:

i. crossing the parental line of NUN 04455 ARA with a second Artichoke plant comprising the single locus conversion, the single trait conversion or the desired trait;

ii. selecting F1 progeny plants that contain the single locus conversion, the single trait conversion or the desired trait;

iii. crossing said selected progeny plants of step ii with the parental line of step i, to produce a backcross progeny plant;

iv. selecting backcross progeny plants comprising the single locus conversion, the single trait conversion or the desired trait and otherwise all or all but one, two or three of the morphological and physiological characteristics the parental line of step i to produce selected backcross progeny plants; and v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to Powdery mildew, *Verticillium* wilt (*V. dahliae*), *Botrytis* rot, Curly Dwarf Virus and Bacterial Crown rotartichoke plume moth (*Platyptilia caduidactyla*), artichoke moth (*Gortyna xantheses*), aphid resistance, proba bug resistance, two-spotted spider-mite resistance, *Chrysanthemum* leaf-miner, and Cribate weevil resistance. Other resistance genes, against pathogenic viruses (e.g. Artichoke Latent Virus, ArLV; artichoke mottled crinkle virus, AMCV; Tomato Spotted Wilt Virus, TSWV; Impatiens necrotic spot virus, INSV; Cucumber mosaic virus, CMV), fungi, bacteria or artichoke pests may also be introduced.

Thus, the invention also provides a combination of parental lines which, when crossed, produce a seed or plant having all physiological and/or morphological characteristics of NUN 04455 ARA but one, two or three which are different (when grown under the same environmental conditions), as well as a seed or plant having all physiological and/or morphological characteristics of NUN 04455 ARA but one, two or three which are different (when the characteristics are determined at the 5% significance level for plants grown under the same conditions).

Also provided is a plant part obtainable from variety NUN 04455 ARA or from progeny of said variety or from a plant having all but one, two or three physiological and/or morphological characteristics which are different from those of NUN 04455 ARA, or from a vegetatively propagated plant of NUN 04455 ARA (or from its progeny or from a plant having all or all but one, two or three physiological and/or morphological characteristics which are different from those of NUN 04455 ARA), being selected from the group consisting of a fruit, a harvested fruit, a part of a fruit, a leaf, a part of a leaf, pollen, an ovule, a cell, a petiole, a shoot or a part thereof, a stem or a part thereof, a root or a part thereof, a root tip, “ovoli”, a cutting, a seed, a part of a seed, seed-coat or another maternal tissue which is part of a seed grown on NUN 04455 ARA, or hypocotyl, cotyledon, a scion, a stock, a rootstock, a pistil, an anther, a flower head or a part thereof, a spine, a bract, a heart, a bottom and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium All documents (e.g., patent publications) are herein incorporated by reference in their entirety.

CITED REFERENCES

Acquaah, Principles of Plant Genetics and Breeding, 2007, Blackwell Publishing, ISBN-13: 978-1-4051-3646-4

Bedini et al, 2012 DOI: 10.2478/s11535-012-0064-xMartin et al. 2008, Australian Journal of Crop Science 1(2): 43-46

Pecaut et al. 1985, Revue Horticuole 256: 21-26)

Pisanu et al. ISHS 2004, Acta Hort. 660

Ryder et al., 1983, Hort Science 18: 646-653

Vos et al. 1995, Nucleic Acid Research 23: 4407-4414

Wijnker et al., Nature Protocols Volume: 9, Pages: 761-772 (2014) DOI: 10.1038/nprot.2014.049

WO2013182646

WO2014076249

EP16199333.2
FAOSTAT, 2013
"Guidelines for the Conduct of Tests for Distinctness, Uniformity and Stability—Artichoke, Cardoon TG/184/4 (Geneva, last revised 2011) world wide web at upov.int/ under edocs/tgdocs/en/tg184.pdf
"OBJECTIVE DESCRIPTION OF VARIETY—Artichoke (*Cynara scolymus* L.)" world wide web at ams.usda.gov/ under resources/st470-artichoke"
Royal Horticultural Society Chart (World Wide Web at rhs.org.uk/Plants/RHS-Publications/RHS-colour-charts)

Example 1

Development of NUN 04455 ARA

The hybrid NUN 04455 ARA was developed from a male and female proprietary inbred line of Nunhems. The female and male parents were crossed to produce hybrid (F1) seeds of NUN 04455 ARA The seeds of NUN 04455 ARA can be grown to produce hybrid plants and parts thereof (e.g. Artichoke head). The hybrid NUN 04455 ARA can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 04455 ARA is uniform and stable.

DEPOSIT INFORMATION

A total of 2500 seeds of the hybrid variety NUN 04455 ARA were deposited according to the Budapest Treaty by Nunhems B.V. on 9 Oct. 2017, at the NCIMB Ltd., Ferguson Building, Craibstone Estate, Bucksburn, Aberdeen AB21 9YA, United Kingdom (NCIMB). The deposit has been assigned NCIMB number 42843. A deposit of NUN 04455 ARA and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

TABLE 1

| UPOV descriptor | Note | Candidate variety NUN 04455 ARA |
|---|---|---|
| Method of maintenance of the variety | 1 hybrid/2 open-pollinated variety/3 parent line 4/other (please specify) | 1 |
| reproduction | 1 seed propagated/2 vegetatively propagated | 1 |
| Plant: height | 1 very short/2 very short to short/3 short/4 short to medium/5 medium/ 6 medium to tall/7 tall/8 tall to very tall/9 very tall | 7 |
| Leaf: attitude | 1 erect/3 semi-erect/5 horizontal | 1 |
| Leaf: long spines | 1 absent/9 present | 1 |
| Leaf: incisions (10th to 12th leaf stage) | 1 absent/9 present | 9 |
| Leaf: intensity of lobing | 3 weak/5 medium/7 strong | 5 |
| Leaf: intensity of lobing | 1 very weak/2 very weak to weak/3 weak/4 weak to medium/5 medium/6 medium to strong/7 strong/8 strong to very strong/9 very strong | 5 |
| Lobe: shape of tip (excluding terminal lobe) | 1 narrow acute/2 broad acute/3 rounded | 3 |
| Lobe: number of secondary lobes | 1 absent or very few/3 few/5 medium/7 many/9 very many | 5 |
| Leaf blade: blistering | 3 weak/5 medium/7 strong | 3 |
| Leaf blade: color | 1 yellow green/2 light green/3 medium green/4 dark green/5 grey green | 3 |
| Midrib: anthocyanin coloration af base | 1 absent or very weak/3 weak/5 medium/7 strong/9 very strong | 7 |
| Midrib: thickness at 35 cm from base | 1 very thin/3 thin/5 medium/7 thick/ 9 very thick | 5 |
| Midrib: length of spines | 1 absent or very short/3 short/5 medium/7 long | 1 |
| Main stem: time of beginning of elongation | 3 early/5 medium/7 late | 5 |
| Main stem: time of beginning of elongation | 1 very early/2 very early to early/3 early/4 early to medium/5 medium/6 medium to late/7 late/8 late to very late/9 late | 6 |
| Main stem: height from base to central flower head | 3 short/5 medium/7 tall | 5 |
| Main stem: height from base to central flower head | 1 very short/2 very short to shortl/3 short/4 short to medium/5 medium/6 medium to tall/7 tall/8 tall to very tall/9 very tall | 6 |

TABLE 1-continued

| UPOV descriptor | Note | Candidate variety NUN 04455 ARA |
|---|---|---|
| Main stem: diameter | 3 small/5 medium/7 large | 5 |
| Main stem: diameter | 1 very small/2 very small to small/3 small/4 small to medium/5 medium/6 medium to large/7 large/8 large to very large/9 very large | 4 |
| Central flower head: length | 3 short/5 medium/7 long | 5 |
| Central flower head: length | 1 very short/2 very short to shortl/3 short/4 short to medium/5 medium/6 medium to long/7 long/8 long to very long/9 very long | 5 |
| Central flower head: diameter | 3 small/5 medium/7 large | 5 |
| Central flower head: diameter | 1 very small/2 very small to small/3 small/4 small to medium/5 medium/6 medium to large/7 large/8 large to very large/9 very large | 4 |
| Central flower head: shape in longitudinal section | 1 triangular/2 ovate/3 oblong/4 circular/5 oblate | 2 |
| Central flower head: shape in longitudinal section | 1 round/2 large elliptical/3 oval/4 triangular/5 transverse broad elliptic | 3 |
| Central flower head: shape of apex | 1 acute/2 rounded/3 flat/4 depressend | 2 |
| Central flower head: time of appearance | 3 early/5 medium/7 late | 5 |
| Central flower head: anthocyanin coloration of inner bracts | 1 absent or very weak/3 weak/5 medium/7 strong/9 very strong | 1 |
| Central flower head: density of inner bracts | 3 sparse/5 medium/7 dense | 7 |
| Receptacle: diameter | 3 small/5 medium/7 large | 3 |
| Receptacle: thickness | 3 thin/5 medium/7 thick | 5 |
| Receptacle: shape in longitudinal section | 1 flat or slightly depressend/2 moderately depressed/3 strongly depressed | 2 |
| Central flower head: time of beginning of opening | 3 early/5 medium/7 late | 5 |
| Outer bract: violet color on external side | 1 absent or very weak/2 weak/3 medium/4 strong/5 very strong | 3 |
| Outer bract: coloration of apex on external side | 1 green/2 bronze/3 grey | 1 |
| Outer bract: colour (external side) | 1 green/2 green with purple/3 purple with green stripes/4 mainly purple/5 completely purple | 2 |
| Outer bract: shape of apex | 1 acute/2 flat/3 emarginate | 3 |
| Outer bract: depth of emargination | 1 shallow/3 medium/5 deep | 3 |
| Outer bract: reflexing of tip | 1 inwards/2 straight/3 outwards | 2 |
| Outer bract: length of spine | 1 absent or very short/3 short/5 medium/7 long | 1 |
| Outer bract: size of spine | 1 absent or very small/3 small/5 medium/7 large/9 very large | 1 |
| Outer bract: mucron | 1 absent/9 present | 1 |
| Outer bract: shape | 1 broader than long/2 as broad as long/3 longer than broad | 3 |
| Outer bract: length of base | 3 short/5 medium/7 long | 7 |
| Outer bract: thickness at base | 1 thin/2 medium/3 thick | 2 |
| Outer bract: thickness at base | 1 absent or very thin/3 thin/5 medium/7 thick/9 very thick | 5 |
| Plant: number of lateral heads on main stem | 1 very few/3 few/5 medium/7 many/9 very many | 7 |
| Main use | 1 fresh market/2 canning/3 ornamental | 2 |
| Main use | 1 fresh market/2 canning/3 industrial use/4 other | 2 |
| if fresh market | 1 large flower head/2 small flower head | 2 |
| if canning | 1 receptacle/2 bottom/3 pickling artichoke | 1 |
| if industrial use | 1 leaf extraction large flower head/2 biomass large flower head | |
| Usage of product | 1 Rootstock/2 Cultural variety | 2 |
| Life cylcle | 1 annual/2 perennial | 1 |
| Other condition | 1 = YES; 2 = NO If yes please provide details | 2 |
| Main use | 1 seed/2 forage/3 garden plant/4 pot plant/5 cut-flower/6 other | 6 |
| | When 6 other please provide details | Normal growing for artichoke production. |
| Commercial production | 1 under cover/2 open field/3 under cover and open field | 2 |

TABLE 1-continued

| UPOV descriptor | Note | Candidate variety NUN 04455 ARA |
|---|---|---|
| Season of growing | 1 spring/2 summer/3 autumn/4 winter | 3-4-1 Harvest from Autumn to the following spring |
| interest of the variety | | Processing market |

Table 1 contains typical values. Values may vary due to environment. Other values that are substantially equivalent are also within the scope of the invention. N.A.=not applicable; n.r.=not recorded.

Example 2: Evaluation of Several Varieties and Comparison Between Number of Heads/Plant Production Field Trials were planted to evaluate the plants comprising the genetic trait for multibranching with the standard varieties during 2012-2013, 2013-2014 and 2014-2015 seasons in La Palma (Cartagena, Spain) and Santa Emilia (Graneros, Chile). Sowing and planting dates are shown in Table 2:

TABLE 2

Sowing and planting dates

| | 2012-2013 | | 2013-2014 | | 2014-2015 | |
|---|---|---|---|---|---|---|
| LOCATION | SOWING DATE | PLANTING DATE | SOWING DATE | PLANTING DATE | SOWING DATE | PLANTING DATE |
| La Palma | 1 Jun. 2012 | 17 Jul. 2012 | 6 Jun. 2013 | 23 Jul. 2013 | 4 Jun. 2014 | 22 Jul. 2014 |
| Santa Emilia | 20 Nov. 2012 | 4 Jan. 2013 | 7 Jan. 2014 | 27 Feb. 2014 | n.r.* | n.r. |

*n.r.: not recorded

Design of the experiment: plots consisted in 20 plants at a planting distance of 2.times.0.8 m. Two randomly selected replications per variety were evaluated. Average head weight and heads per plant were recorded in 2012-13 trial; and average head weight, average heads per plant and average head diameter were recorded in 2013-2014 in Spain. In Chile, only the number of heads per plant were recorded during 2012-2013 and average head weight and heads per plant were recorded during 2013-2014 season. The evaluated varieties were NUN 04455 ARA (comprising the genetic determinant for multibranching (M allele) and the genetic determinant for enhanced multibranching (E allele)) and Madrigal and Symphony as comparison. Results are shown in Tables 3-6.

TABLE 3

Average production of heads per plant

| LOCATION | VARIETY | 2012-2013 | 2013-2014 | 2014-2015 |
|---|---|---|---|---|
| La Palma | Madrigal | 8.9 | 13.0 | 17.2 |
| La Palma | Symphony | 9.95 | 15.6 | 21.2 |
| La Palma | NUN 04455 ARA | 20.15 | 16.75 | 34.6 |
| Santa Emilia | Madrigal | 14.5 | 9.9 | |
| Santa Emilia | Symphony | 13.95 | 11.4 | |
| Santa Emilia | NUN 04455 ARA | 24.3 | 22.9 | |

TABLE 4

Average weight per head (g)

| LOCATION | VARIETY | 2012-2013 | 2013-2014 | 2014-2015 |
|---|---|---|---|---|
| La Palma | Madrigal | 263.2 | 162.3 | 137.6 |
| La Palma | Symphony | 202.5 | 147.6 | 123.6 |
| La Palma | NUN 04455 ARA | 177.6 | 102.9 | 95.8 |
| Santa Emilia | Madrigal | | 205.2 | |
| Santa Emilia | Symphony | | 230.9 | |
| Santa Emilia | NUN 04455 ARA | | 114.9 | |

TABLE 5

Average diameter per head (mm)

| LOCATION | VARIETY | 2013-2014 | 2014-2015 |
|---|---|---|---|
| La Palma | Madrigal (comparisson) | 70.1 | 66.4 |
| La Palma | Symphony (comparisson) | 68.5 | 62.1 |
| La Palma | NUN 04455 ARA | 63.4 | 56.5 |

TABLE 6

Total yield per Ha (Tons)

| LOCATION | VARIETY | 2013-2014 | 2014-2015 |
|---|---|---|---|
| La Palma | Madrigal | 16.01 | 15.08 |
| La Palma | Symphony | 17.08 | 18.20 |
| La Palma | NUN 04455 ARA | 14.16 | 19.21 |

What is claimed is:

1. A hybrid plant, plant part or seed of Artichoke variety NUN 04455 ARA, wherein a representative sample of seed of said variety is deposited under Accession Number NCIMB 42843.

2. The plant part of claim 1, wherein the plant part is a leaf, pollen, an ovule, a fruit, a scion, a root, an ovoli, a rootstock, cutting, a flower head, a spine, a bract, a heart, a bottom, a flower or a part of any of these or a cell.

3. A seed that produces the plant of claim 1.

4. A seed grown on the plant of claim 1.

5. A tissue or cell culture comprising cells of the plant of claim 1.

6. The tissue or cell culture according to claim 5, comprising cells or protoplasts derived from a plant part, wherein the plant part is an embryo, a meristem, a cotyledon, a hypocotyl, pollen, a leaf, an anther, a root, an ovoli, a root tip, a pistil, a petiole, a flower head, a spine, a bract, a heart, a bottom flower, fruit, seed, a stem or a stalk.

7. An F1 Artichoke plant regenerated from the tissue or cell culture of claim 6 or claim 5, wherein the plant has all of the physiological and morphological characteristics of the plant of NUN 04455 ARA when grown under the same environmental conditions, and wherein a representative sample of seed of NUN 04455 ARA is deposited under Accession Number NCIMB 42843.

8. A method of producing the plant of claim 1, comprising vegetative propagation of at least a part of NUN 04455 ARA, wherein a representative sample of seed of said variety is deposited under Accession Number NCIMB 42843.

9. The method of claim 8, wherein said vegetative propagation comprises regenerating a whole plant from said part of NUN 04455 ARA, wherein a representative sample of seed of said variety is deposited under Accession Number NCIMB 42843.

10. The method of claim 8, wherein said part is a cutting, a cell culture or a tissue culture.

11. An F1 vegetative propagated plant, or a part of said propagated plant, propagated from the plant of claim 1 or the plant part of claim 2 wherein the vegetative propagated plant has all of the physiological and morphological characteristics of the plant of NUN 04455 ARA, when grown under the same conditions, and wherein a representative sample of seed of NUN 04455 ARA is deposited under Accession Number NCIMB 42843.

12. A method of producing an Artichoke plant, comprising crossing the plant of claim 1 with a second Artichoke plant at least once, allowing the progeny to form seed and optionally selecting progeny from said crossing.

13. The F1 plant of claim 1 further comprising a single locus conversion, wherein said plant has all of the morphological and physiological characteristics of the plant of NUN 04455 ARA when grown under the same environmental conditions and, wherein a representative sample of seed of said variety is deposited under Accession Number NCIMB 42843, optionally wherein the single locus conversion confers a trait selected from the group consisting of male sterility, herbicide tolerance, insect resistance, pest resistance, disease resistance, environmental stress tolerance, modified carbohydrate metabolism and modified protein metabolism, wherein the plant is an F1 plant.

14. A method of making doubled haploids of Artichoke variety NUN 04455 ARA, comprising making double haploid cells from haploid cells from Artichoke variety NUN 04455 ARA or a seed of claim 1, wherein a representative sample of seed of Artichoke variety NUN 04455 ARA is deposited under Accession Number NCIMB 42843, and wherein the doubled haploid cells have all the physiological and morphological characteristics of Artichoke variety NUN 04455 ARA.

15. A container comprising a plant, plant part or seed of claim 1.

16. A food or feed product or a processed product comprising at least one cell of claim 2.

17. A method of producing an Artichoke flower head, comprising:
   a. growing a plant of claim 1 until it develops at least one flower head; and
   b. collecting the flower head of step a).

* * * * *